United States Patent
Gitel

(10) Patent No.: US 7,544,514 B2
(45) Date of Patent: Jun. 9, 2009

(54) METHOD AND SYSTEM FOR DETERMINING PLATELET-MEDIATED CLOT FORMATION

(75) Inventor: Sanford N. Gitel, Netania (IL)

(73) Assignees: David Varon, Kfar Bilu A (IL); Ramot at Tel-Aviv University Ltd., Tel Aviv (IL)

( * ) Notice: Subject to any disclaimer, the term of this patent is extended or adjusted under 35 U.S.C. 154(b) by 806 days.

(21) Appl. No.: 11/022,339

(22) Filed: Dec. 27, 2004

(65) Prior Publication Data

US 2006/0141629 A1    Jun. 29, 2006

(51) Int. Cl.
*G01N 33/86* (2006.01)
*G01N 33/48* (2006.01)

(52) U.S. Cl. .............. 436/69; 436/63; 422/73; 600/369; 73/64.41

(58) Field of Classification Search .......... 436/63, 436/69, 174; 422/73; 435/2; 600/369; 73/64.41, 73/64.43
See application file for complete search history.

(56) References Cited

U.S. PATENT DOCUMENTS

| | | | | |
|---|---|---|---|---|
| 5,184,188 | A * | 2/1993 | Bull et al. | 356/39 |
| 5,523,238 | A | 6/1996 | Varon et al. | |
| 6,043,871 | A * | 3/2000 | Solen et al. | 356/39 |
| 6,410,337 | B1 * | 6/2002 | Brady et al. | 436/69 |
| 6,537,819 | B2 * | 3/2003 | Cohen et al. | 436/69 |
| 6,573,104 | B2 * | 6/2003 | Carr et al. | 436/69 |
| 6,872,572 | B2 * | 3/2005 | Brady et al. | 436/69 |
| 6,989,272 | B1 * | 1/2006 | Savion et al. | 436/46 |
| 7,179,652 | B2 * | 2/2007 | Cohen et al. | 436/69 |
| 7,223,365 | B2 * | 5/2007 | Freiherr Von Der Goltz | 422/68.1 |
| 7,262,059 | B2 * | 8/2007 | Zheng et al. | 436/69 |
| 7,309,607 | B2 * | 12/2007 | Ericson | 436/69 |
| 7,361,306 | B2 * | 4/2008 | Bote Bote | 422/73 |
| 7,393,690 | B2 * | 7/2008 | Sukavaneshvar et al. | 436/69 |
| 2004/0131500 | A1 * | 7/2004 | Chow | 422/72 |
| 2005/0202566 | A1 * | 9/2005 | Frojmovic | 436/63 |

FOREIGN PATENT DOCUMENTS

GB    1 224 355    9/1971

OTHER PUBLICATIONS

Hoffman, R., et al., eds., *Hematology*, 2nd. Ed., Churchhill Livingstone, Ch. 100, pp. 1569, (1995).
Michelson, A.D., ed., *Platelets*, Academic Press, Fig. 14-1, (2002).
Varon, D., et al., "Cone and Plate(let) Analyzer: Monitoring Glycoprotein IIb/IIIa Antagonists and Von Willebrand Disease Replacement Therapy by Testing Platelet Deposition Under Flow Conditions", *American Heart Journal*, p. 188-193, (May 1998).

* cited by examiner

*Primary Examiner*—Maureen M Wallenhorst
(74) *Attorney, Agent, or Firm*—The Nath Law Group; Susanne M. Hopkins; Ari G. Zytcer

(57) ABSTRACT

The present subject matter concerns methods for determining platelet medicated clot formation. Specifically, the subject matter provides a method for determining platelet-medicated clot formation in a blood sample. The method may include obtaining sample of blood, and optionally mixing same with an anti-coagulant in an amount effective to inhibit clot formation. Additionally, the method may include mixing the sample in a vessel with a minute amount of an initiator to obtain a mixed sample, the amount being effective to initiate coagulation. The method may further include rotating the mixed sample inside the vessel, whereby shear forces are developed at the surface of the vessel in a manner and for a time sufficient to allow adhesion of platelets at the surface of the vessel. In addition, the method may include determining clot formation at the surface of the adherent platelets.

14 Claims, 7 Drawing Sheets

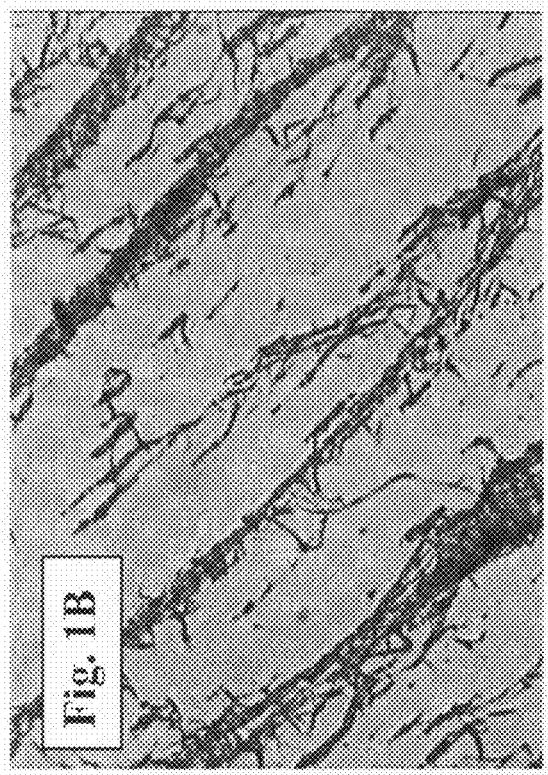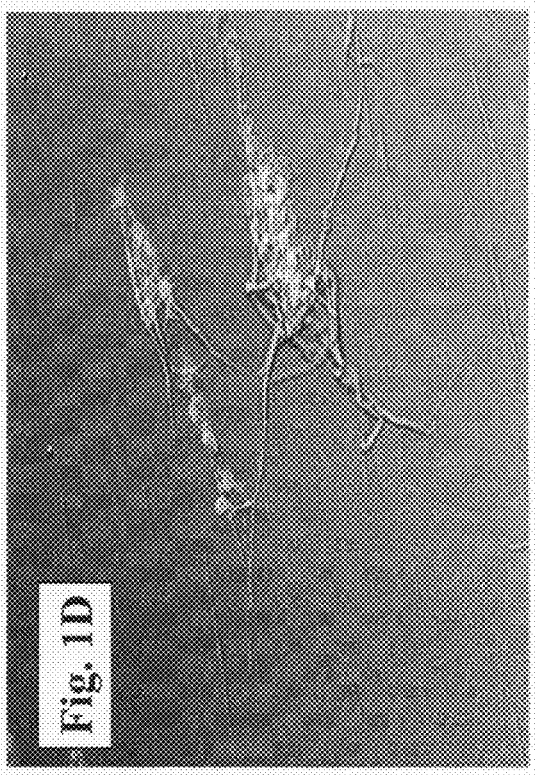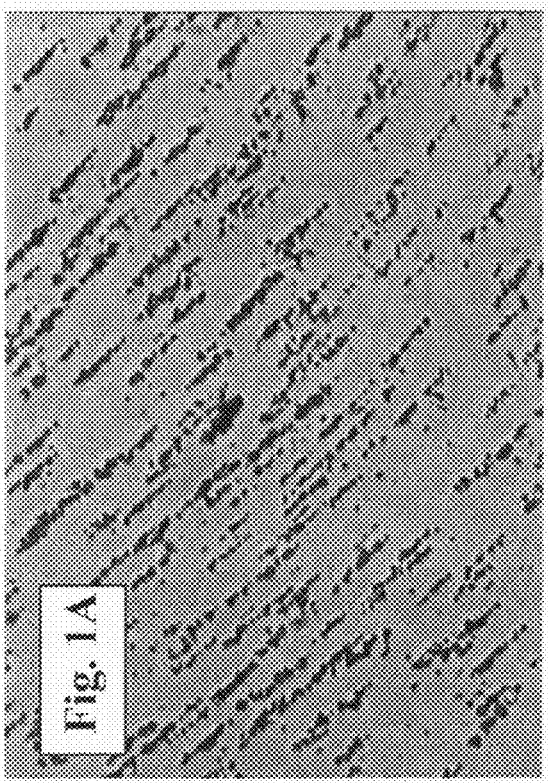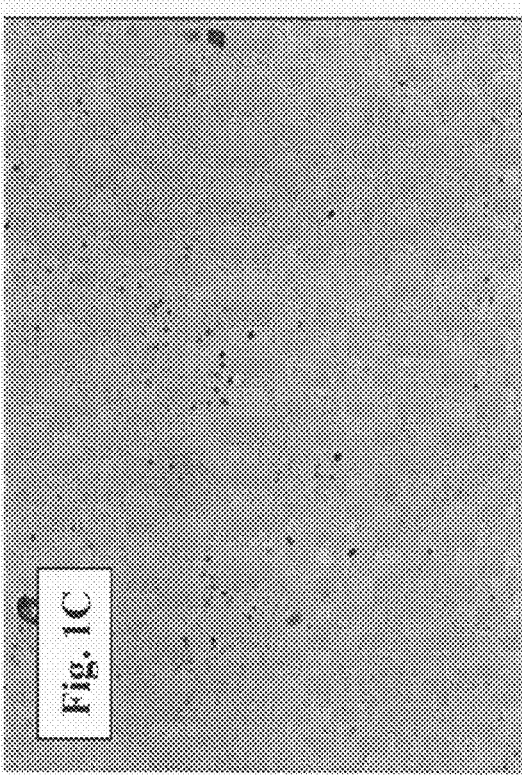

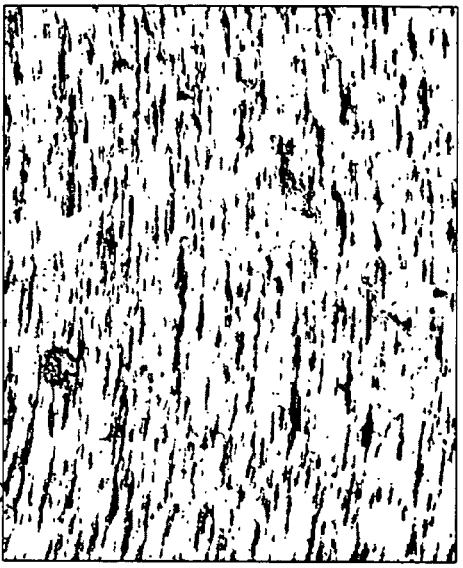
Fig. 3A SC 7.4%; AS 45
Basic
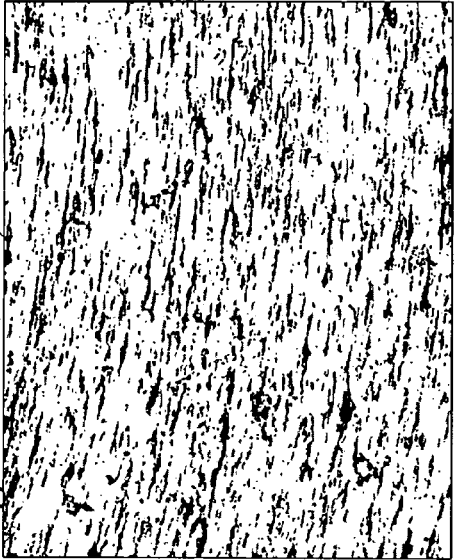
Fig. 3B SC 18.4%; AS 104
Control + DiaCelin
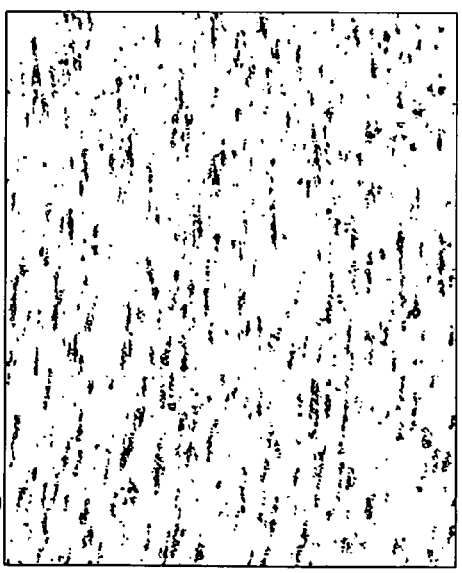
Fig. 3C SC 6.3%; AS 36
Hemophilia + DiaCelin
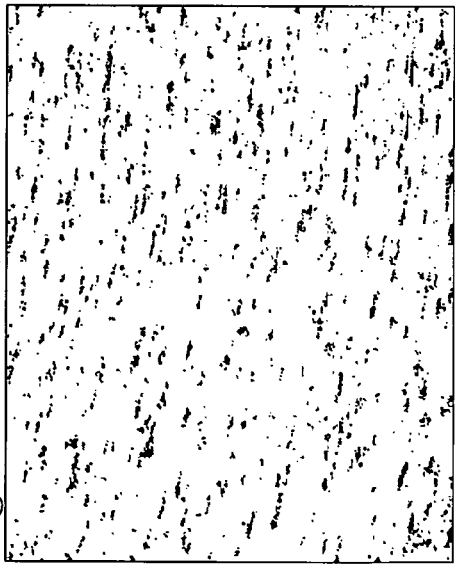
Fig. 3D SC 21.3%; AS 74
Hemophilia + heamateP+DiaCelin

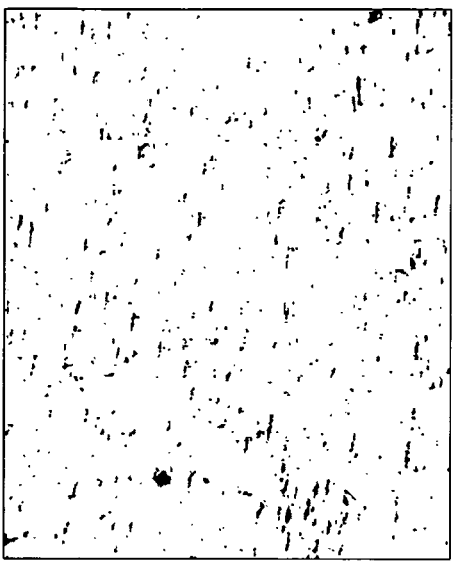
Fig. 4B Control 3.8 µl PT Diluted
SC 14.3%  AS 115
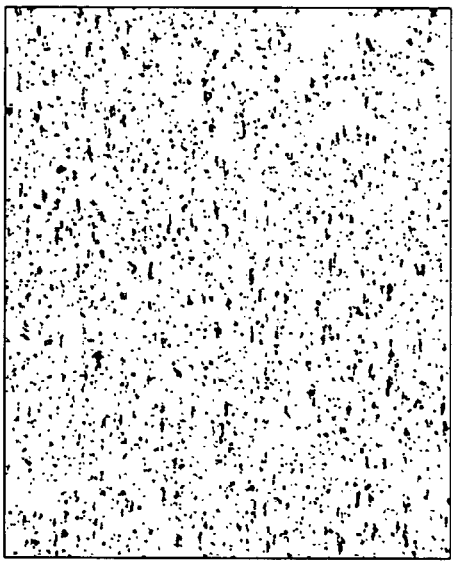
Fig. 4D Patient 4.0 µl PT Diluted
SC 3.0%  AS 30
Fig. 4A Control INR 1.3
SC 9.8%  AS 38
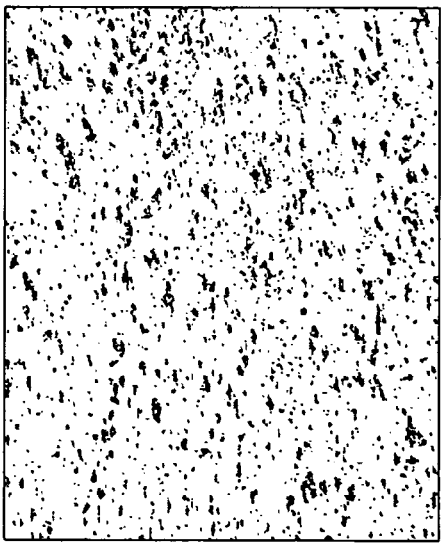
Fig. 4C Patient INR 3.0
SC 8.2%  AS 24

Fig. 5A Control
SC 8.2% AS 27
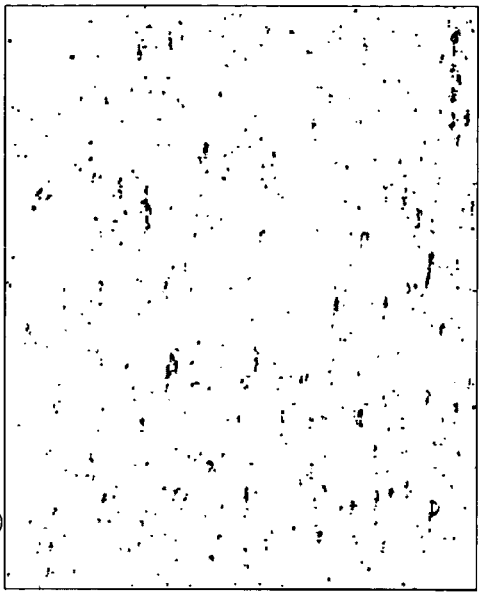
Fig. 5B Control with $1.5 \times 10^{-4}$ units Xa
SC 13.4% AS 118
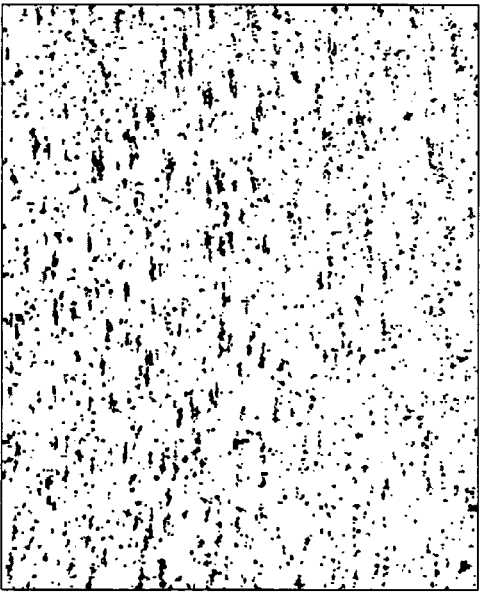
Fig. 5C Patient with heparin (PTT=130")
SC 11.9% AS 44
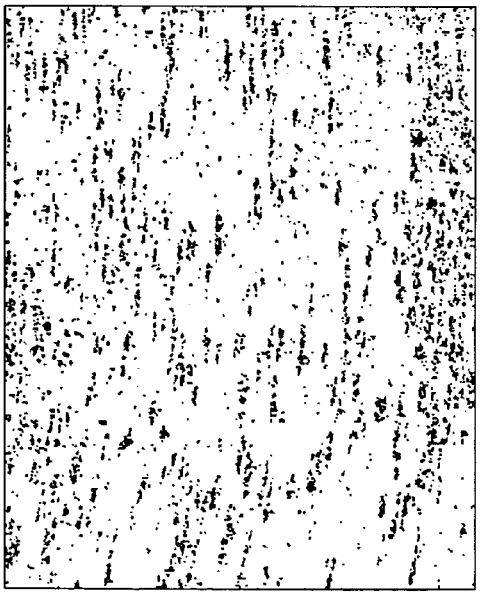
Fig. 5D Patient with $1.5 \times 10^{-4}$ units Xa
SC 6.6% AS 53

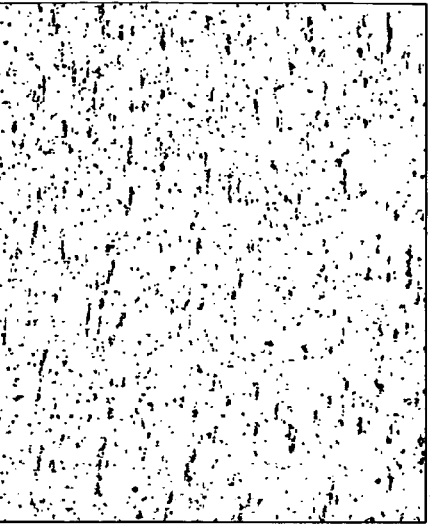
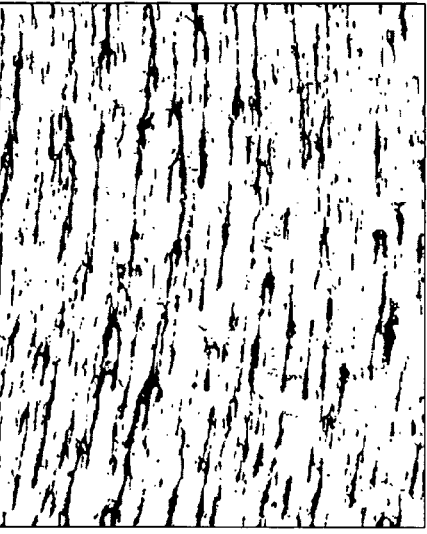
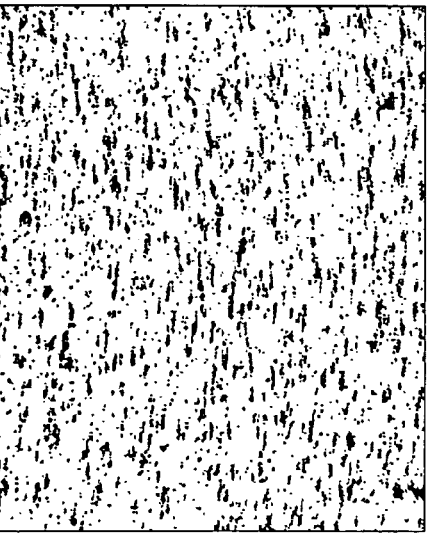

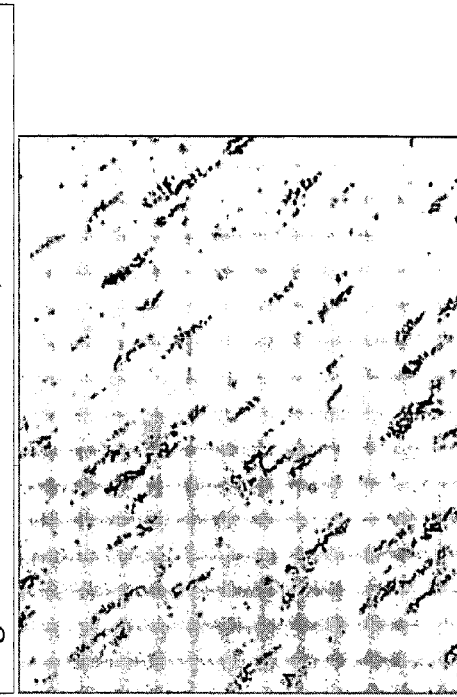
Fig 7A Control  S.C. 5.5% A.S. 22.5
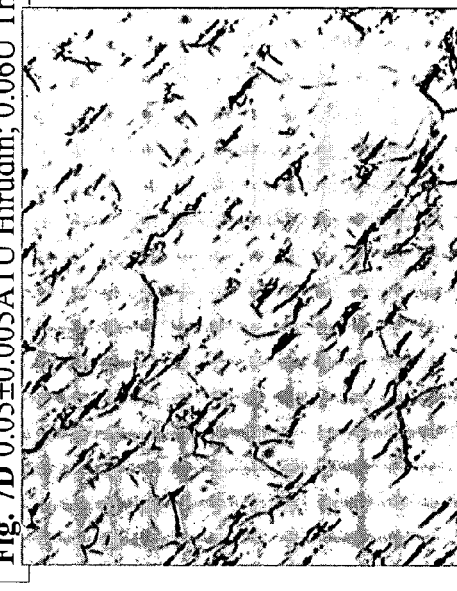
Fig. 7C 0.01U Thrombin  S.C. 6.7% A.S. 31.5
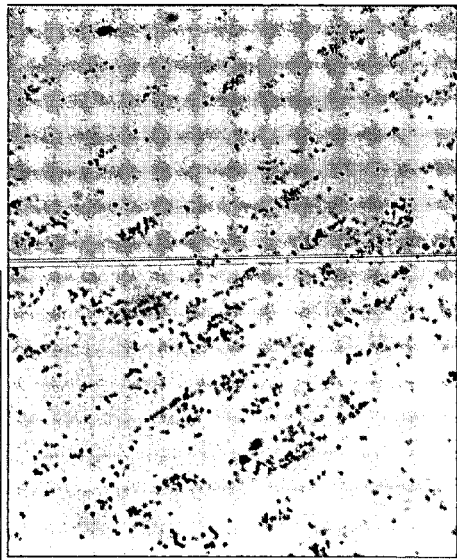
Fig 7B 0.05±0.005ATU Hirudin; 0.04U Thrombin  S.C. 5.0% A.S. 24.7
Fig. 7D 0.05±0.005ATU Hirudin; 0.06U Thrombin  S.C. 9.8% A.S. 30.4

METHOD AND SYSTEM FOR DETERMINING PLATELET-MEDIATED CLOT FORMATION

FIELD OF THE INVENTION

The present invention concerns thrombosis and hemostasis and more specifically methods of diagnosing and treating coagulation disorders.

BACKGROUND OF THE INVENTION

When a wound occurs, several changes take place to minimize blood loss, referred to as the hemostatic response. First, the blood vessels slow the flow of blood past the wound site. Next, platelets that circulate in the blood are collected at the wound site to form a plug. Finally, a second system (the coagulation cascade), based upon the action of multiple proteins (called clotting factors) that act in concert to produce a fibrin clot is activated. These two systems (also known by the terms "primary hemostasis" and "secondary hemostasis") work in concert to form a clot. Disorders in either system can yield conditions that cause either too much or too little clotting.

Platelets serve three primary functions. When a break in a blood vessel occurs, substances are exposed that normally are not in direct contact with the blood flow. These substances (primarily collagen and immobilized von Willebrand factor) allow the platelets to adhere to the broken surface ($1^{st}$ function). Once a platelet adheres to the surface, it releases chemicals that attract additional platelets to the damaged area, referred to as platelet aggregation (2nd function). These two processes are the first responses to stop bleeding. The platelet aggregates then serve as support for the processes of the coagulation cascade ($3^{rd}$ function). The protein based system (the coagulation cascade) serves to stabilize the clot that has formed and further seal up the wound.

The goal of the coagulation cascade (the "secondary hemostasis") is to form a fibrin mesh within the platelet aggregate to stabilize the clot. All of the clotting factors have an inactive and an active form. Once activated, the factor will serve to activate the next factor in the sequence until fibrin is formed.

The many reactions in the coagulation cascade that are necessary to form a clot are described [Hematology—basic principles and practice, editors: Hoffman R, Benz E J, Shattil S J, Furie B, Cohen H J, Silberstein L E Churchill Livingstone 1995, P-1569]

The coagulation cascade is a chain of enzymatic reactions leading to the formation of a fibrin (F) clot [Platelets, Editor Michelson A D, Academic Press 2002, P-230]. The physiological cascade is initiated at the extrinsic pathway, by the exposure of tissue factor (TF), at the site of vessel injury or on activated blood cells (endothelial cells, monocytes etc). Tissue factor forms a complex with factor FVII, converting to it's activated form (FVIIa). This complex is then capable of activating factors X (FX), by creating a complex known as the "extrinsic tenase"), and factor IX (FIX). These activated factors (FIXa and FXa), then continue the enzymatic cascade at both the intrinsic (FIXa) and the common (FXa) pathways. Factor Xa forms a complex with prothrombin (PT), activated factor V (FVa) and phospholipids (derived from activated platelets), in the presence of calcium (this complex is termed "prothrombinase"), leading to activation of prothrombin to thrombin (T). Thrombin is a key player in the coagulation cascade, promoting many steps including: a) cleaving of fibrinogen (FG) to fibrin (F) monomers, which then spontaneously form polymers, b) activating factor XIII which cross-links fibrin polymers to create an insoluble fibrin clot, c) promoting the intrinsic cascade in a positive feedback loop by activating FXI, FVIII and FV, and d) activating platelets.

The intrinsic pathway is initiated by the activation of Factor XI (FXI) leading to activation of FIX, which then forms a complex with FX, Factor VIIIa (FVIIIa) and phospholipids, in the presence of calcium (known as the "intrinsic tenase" complex). This complex leads to the activation of Factor X (FXa), which then continues the reaction to the prothrombinase step (the common pathway).

The coagulation cascade is controlled by natural anticoagulants that inhibit different steps of the reaction. Thus antithrombin III (ATIII), inhibits mostly thrombin and Factor Xa, by creating a complex that prevents their enzymatic function. This effect is mediated by heparin, which activates ATIII and assembles the two proteins, allowing a better anticoagulant effect.

Another anticoagulant pathway includes protein C (PC) and protein S (PS), cooperatively capable of cleaving Factor V and Factor VIII, thus inhibiting the tenase and the prothrombinase steps.

Activated platelets express on their surface negatively charge phospholipids, that allow the assembly of coagulation factors leading to the creation of these complexes. The formation of these complexes (the intrinsic and extrinsic tenase as well as the ptothrombinase), increase significantly the rate of the coagulation reaction, by enhancing the interaction of the closely assembled clotting factors on the platelet membrane. Thus physiological clot formation is produced mostly on the surface of activated platelets, which are the first to adhere and aggregate at the site of the injured vessel wall.

The different factors involved in clot formation may be categorized as those which facilitate clot formation and those which block clot formation.

Blood clotting disorders may be divided into those related to platelet disorders, and those related to coagulation cascade disorders. If the clotting system can not adequately form clots, then the result is a bleeding disorder (hemophilia); if the clotting system forms clots too easily, then the result is formation of excess clots (thrombophilia).

Platelet disorders occur when there are too few platelets, too many platelets or a normal number of platelets that do not function in the normal manner. Having too few platelet or platelets that do not function well (for example, aspirin use) can lead to a bleeding tendency. Likewise, too many platelets can predispose to a tendency to clot excessively.

The coagulation cascade also has the potential to cause both an inability to form clots (hemophilia) and an excessive ability to form clots (thrombophilia). Hemophilic states result when there are decreased levels of the clotting factors. There are two primary disorders, hemophilia A and hemophilia B. Hemophilia A results from low levels of factor VIII and hemophilia B results from low levels of factor IX. Low levels of virtually any of the factors (with the exception of factor XII) will result in an inability to form blood clots; and thus, excess bleeding.

Hereditary bleeding disorders other than hemophilia may occur due to deficiencies or defects in other specific clotting factors. They are diagnosed by specific laboratory studies and treated by factor replacement.

Deficiencies in other factors, such as V, VII, X, and XIII, are rarer than the hemophilias, but produce similar symptoms. Factor XI deficiency is a common bleeding disorder among Ashkenazic Jews' affecting about 10% of them. Diagnosis depends on detection of bleeding symptoms, family history, and laboratory testing. Treatment usually involves blood transfusions, especially replacement of the missing coagulation factor, medications such as desmopressin (DDAVP), and antifibrolytic medications such as ∈-aminocaproic acid (Amicar), and tranexamic acid (TA).

Hereditary von Willebrand's disease is an inherited bleeding disorder that affects the von Willebrand factor (vWf), which is necessary for platelet function and for fibrin clot formation. In von Willebrand's disease, there is a defect in the body's ability to produce vWf. This results in excessive bleeding from the mucus membrane of body cavities, such as the nose, the uterus, the bladder, and the rectum.

Another coagulation disorder is dysfibrinogenemia. Fibrinogen is the molecule that eventually becomes a fibrin, the major blood clotting protein. Fibrinogen is produced in the liver and bone marrow and released into the blood and eventually becomes fibrin. Dysfibrinogenemia is produced by an inherited problem in fibrinogen production. Abnormal fibrinogen is produced, leading to clotting problems in some individuals.

U.S. Pat. No. 5,523,238 describes a method and apparatus for determining platelet function in primary hemostasis. The method comprises obtaining a whole blood sample or platelet containing fraction of the blood (optionally mixed with an anticoagulant) and introducing the sample into a vessel having a flat bottom, the inner surface of which is covered with a substrate capable of inducing platelet adhesion to the surface and aggregation. The mixture inside the vessel is rotated such that a shear force is developed at the surface of the vessel. Then, parameters associated with primary hemostasis are determined. Such parameters include, inter alia, the amount of adhered platelets, aggregates size, aggregates' morphology, total area covered by the aggregates and size distribution of adhered platelets or aggregates.

SUMMARY OF INVENTION

According to a first aspect, the present invention provides a method for determining platelet-medicated clot formation in a blood sample comprising:
(a) obtaining sample of blood, and optionally mixing same with an anti-coagulant in an amount effective to inhibit clot formation;
(b) in a vessel, mixing the sample with a minute amount of an initiator to obtain a mixed sample, the amount being effective to initiate coagulation;
(c) rotating the mixed sample inside the vessel, whereby shear forces are developed at the surface of said vessel in a manner and for a time sufficient to allow adhesion of platelets at the surface of said vessel;
(d) determining clot formation at the surface of said adherent platelets.

According to this aspect, the invention may be applied for determining a coagulation disorder in a subject having a coagulation factor dysfunction, the method comprising:
(a) obtaining from said subject a test sample of blood, and optionally mixing same with an anti-coagulant in an amount effective to inhibit clot formation;
(b) in a vessel, mixing the sample with a minute amount of an initiator to obtain a mixed sample, the amount being sufficient to initiate coagulation;
(c) rotating the mixed sample inside the vessel, whereby shear forces are developed at the surface of said vessel in a manner and for a time sufficient to allow adhesion of platelets at the surface of said vessel;
(d) determining clot formation associated with the surface of said adherent platelets;
whereby a significant abnormal fibrin clot formation at said surface of adhered platelets indicating that said subject has a coagulation factor dysfunction.

According to a second aspect, the present invention provides a method for identifying a coagulation effector dysfunction in a subject having a coagulation disorder, the method comprising:
(a) obtaining from said subject a sample of blood, and optionally adding to said sample an anti-coagulant in an amount sufficient to inhibit clot formation;
(b) in a vessel, mixing the sample with a minute amount of an initiator to obtain a mixed sample, the amount being effective to initiate clot formation;
(c) adding to said mixed sample an amount of a coagulation effector selected from a coagulation factor, activated coagulation inhibitor, a component of a coagulation inhibitor and activator of a coagulation inhibitor suspected to be deficient in the sample, to obtain a treated sample, the amount being sufficient to affect platelet-mediated fibrin clot formation;
(d) rotating said treated sample inside the vessel, whereby shear forces are developed at the surface of said vessel in a manner and for a time sufficient to allow adhesion of platelets at the surface of said vessel;
(e) determining platelet-mediated fibrin clot formation at the surface of said adherent platelets.

According to this aspect, when said coagulation effector is a coagulation factor, the method includes determining an increase in platelet mediated fibrin clot formation, where:
i) a significant increase in fibrin clots formed at said surface as compared with a reference sample (lacking the added factor), indicates that said disorder is associated with a deficiency in said coagulation factor;
ii) an insignificant increase in fibrin clots formed at said surface as compared with a reference sample indicates that said disorder is associated with a deficiency in a another coagulation factor.

According to this aspect, when said coagulation effector is an activated coagulation inhibitor, a component of a coagulation inhibitor or an activator of a coagulation inhibitor, the method includes determining a decrease in platelet mediated fibrin clot formation, where:
an insignificant decrease in clots formed at said surface as compared to a reference sample (lacking the above added inhibitor), indicates that said disorder is associates with an abnormal response to said effector.

According to yet another aspect, the invention provides a method for monitoring blood concentration of an anti-thrombotic drug, the method comprises:
(a) obtaining from said subject a sample of blood;
(b) in vessels, titrating said sample with increasing amounts of a drug counter reagent;
(c) rotating the titrated sample in said vessels, whereby shear forces are developed at the surface of the vessel in a manner and for a time sufficient to allow adhesion of platelets at the surface of said vessel;
(d) determining a titration curve for said drug counter reagent, the titration curve defining a parameter associated with clot formation as a function of concentration of the drug-counter reagent;
(e) determining from said titration curve blood concentration of said anti-thrombotic drug.

According to a fifth aspect, the invention provides a method for designing treatment of a subject with a coagulation factor, said subject having a coagulation disorder (clotting factor deficiency), the method comprising:
(a) obtaining from said subject a sample of blood;
(b) in vessels, titrating said sample with increasing concentrations of a coagulation factor;

(c) rotating the titrated sample in said vessels, whereby shear forces are developed at the surface of the vessel in a manner and for a time sufficient to allow adhesion of platelets at the surface of said vessel;

(d) determining a titration curve for said coagulation factor, the titration curve defining a parameter associated with clot formation as a function of concentration of the coagulation factor;

(e) designing treatment of said subject based on said titration curve.

DESCRIPTION OF THE FIGURES

FIG. 1A-1D are microscope images of a blood sample under different conditions, tested by the method and system of the invention: FIG. 1A shows a typical field of platelets adhered and aggregated on the surface indicating the formation of primary hemostasis; FIG. 1B shows fibrin clot formation upon addition of a clot initiator, in this particular embodiment, activated factor X (factor Xa); FIG. 1C shows that no coagulation occurs in a thrombocytopenic blood sample; FIG. 1D shows a confocal microscope image of a fibrin clot associated with adherent platelet aggregate. The platelets were stained by monoclonal anti-GPIIb antibody (Dako, Glostrup, Denmark) followed by FITC-conjugated second antibody.

FIG. 3A-3D show the effect of aPTT reagent Diacelin (Diamed) and $CaCl_2$ on fibrin clot formation in whole blood from a healthy subject as well as from hemophilia patients: FIG. 3A shows the results when no aPTT reagent or $CaCl_2$ is added to blood from a healthy subject; FIG. 3B shows the results when aPTT reagent [DiaCelin (DiaMed, Switzerland) 2-4 µl/130 µl reaction volume] and $CaCl_2$ (12 mM) are added to blood from a healthy subject; FIG. 3C shows the results with blood from hemophilia patient, the blood being treated with aPTT reagent [DiaCelin (DiaMed, Switzerland) 2-4 µl/130 µl reaction volume] and $CaCl_2$ (12 mM); FIG. 3D shows the results when Hemate-P (a factor VIII concentrate) is added to the blood of the hemophilia patient to obtain a factor VIII level of about 1 U/ml prior to the addition of aPTT reagent and $CaCl_2$.

FIG. 4A-4D show the effect of PT-fibrinogen reagent (Instrumentation Laboratories) and $CaCl_2$ on fibrin clot formation in whole blood from healthy subjects as well as from patients receiving coumadin therapy: FIG. 4A shows the results when no PT-fibrinogen reagent and $CaCl_2$ is added to the blood from a healthy subject; FIG. 4B shows the results when PT-fibrinogen reagent (0.4-0.5 µl/130 µl reaction volume] and $CaCl_2$ (12 mM) is added to blood from a healthy subject; FIG. 4C shows the results with blood from patients receiving coumadin therapy, in the absence of PT-fibrinogen reagent and $CaCl_2$; and FIG. 4D shows the results with blood from patients receiving coumadin therapy, the blood being supplemented with PT-fibrinogen reagent and $CaCl_2$ as in FIG. 5B.

FIG. 5A-5D show the effect of factor Xa and $CaCl_2$ on clot formation in healthy subjects as well as in patients receiving heparin therapy: FIG. 5A shows the results when no factor Xa or $CaCl_2$ are added to blood from a healthy subject; FIG. 5B shows the results when blood from a healthy subject is treated with factor Xa ($1.5 \times 10^{-4}$ Units/ml) and $CaCl_2$ (12 mM); FIG. 5C shows the results when no factor Xa or $CaCl_2$ are added to blood from a patient receiving heparin therapy (PTT=130 sec, normal range 26-34 sec); FIG. 5D shows the results when blood from this patient was supplemented with factor Xa ($1.5 \times 10^{-4}$ Units/ml) and $CaCl_2$ (12 mM).

FIG. 6A-6F show the effect of synthetic factor Xa inhibitors on fibrin clot formation and a titration assay for determining the level of this inhibitor in whole blood: FIG. 6A shows the results when no factor Xa or $CaCl_2$ was added to blood from a healthy subject; FIG. 6B shows the results when factor Xa ($1 \times 10^{-3}$ Units/ml) and $CaCl_2$ (12 mM) were added to blood from this healthy subject; FIG. 6C shows the results when factor Xa ($1 \times 10^{-3}$ Units/ml) and $CaCl_2$ (12 mM) were added to blood from a patient treated orally with anti-factor Xa drug; FIG. 6D shows the results when a higher concentration of factor Xa ($4.5 \times 10^{-1}$ Units/ml) and $CaCl_2$ (12 mM) were added to the anti-factor Xa treated blood; FIG. 6E shows the results when factor Xa ($5.8 \times 10^{-1}$ Units/ml) and $CaCl_2$ (12 mM) were added to the anti-factor Xa treated blood; FIG. 6F shows the results when factor Xa ($6.4 \times 10^{-1}$ Units/ml) and $CaCl_2$ (12 mM) were added to the anti-factor Xa treated blood.

FIG. 7A-7D show a titration assay for determining the levels of specific thrombin inhibitors, in this particular embodiment, hirudin, in whole blood: FIG. 7A shows results when no hirudin or thrombin are added to whole blood from healthy subjects; FIG. 7B shows results when thrombin ($4 \times 10^{-2}$ Units/ml) was added to whole blood treated with hirudin ($5 \times 10^{-2}$ antithrombin Units/ml); FIG. 7C shows the results when thrombin ($1 \times 10^{-2}$ Units/ml) was added to whole blood treated with hirudin ($5 \times 10^{-2}$ antithrombin Units/ml); FIG. 7D shows the results when thrombin ($6 \times 10^{-2}$ Units/ml) was added to whole blood treated with hirudin ($5 \times 10^{-2}$ antithrombin Units/ml).

DETAILED DESCRIPTION OF THE INVENTION

Figure 2A:
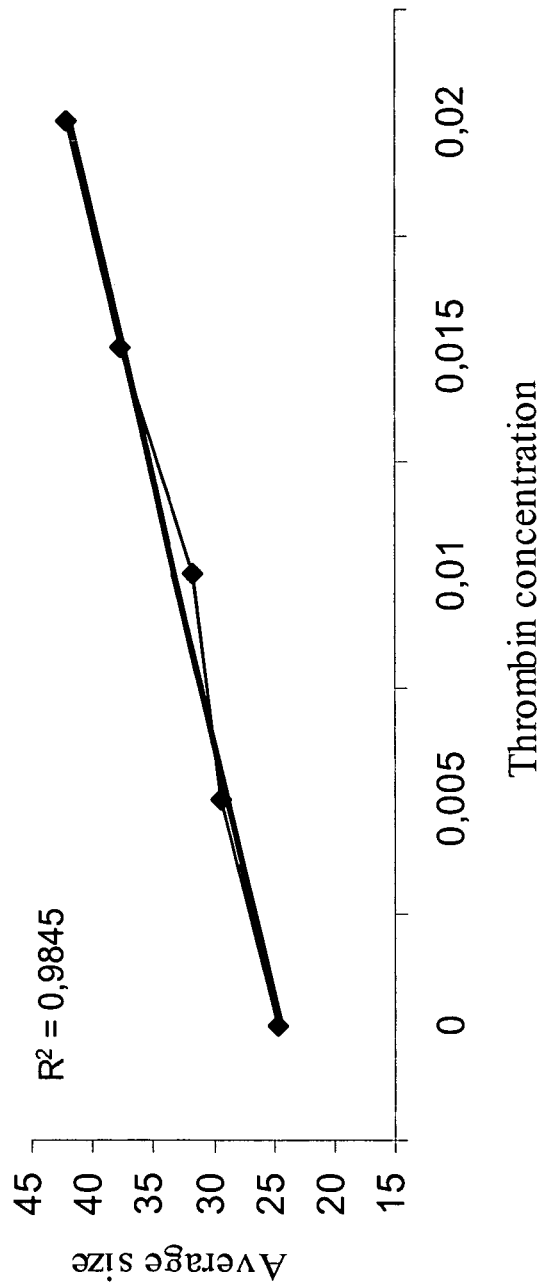
FIG. 2A-2B show a dose response of fibrin clot formation to thrombin added to a blood sample. In response to the addition of thrombin to a tested sample the average size (FIG. 2A) and surface coverage (FIG. 2B) increase as a result of fibrin clots associated with adherent platelets. The sensitivity of the system is demonstrated by the sharp increase in both average size and surface coverage upon addition of only 0.005 IU/ml of thrombin.

According to one embodiment, the method of the invention is executed by the use of a Cone and Platelet Analyzer (CPA). The structure of one such analyzer is described in WO02/071037. In general, the CPA includes an apparatus having a cone-plate device comprising a cylindrical vessel and a rotating element, a bottom portion having the shape of an inverted cone. The bottom surface of the vessel may be covered by an extracellular matrix (ECM).

The present invention is based a Cone and Plate(let) Analyzer (CPA) described in U.S. Pat. No. 5,523,238, incorporated herein by reference. In general, the CPA includes an apparatus having a cone-plate device comprising a cylindrical vessel and a rotating element, a bottom portion having the shape of an inverted cone. FIG. 1 is a schematic representation of an apparatus which may be used in accordance with the invention. The apparatus comprises a cone-plate device 10 comprising a polystyrene cylindrical vessel 11 and a rotating element 12 having a bottom portion 13 having the shape of an inverted cone. The rotating element 12 holds inside a magnetic bar 14. The upper portion 15 of the element 12 is held inside stopper 16, whereby element 12 is suspended from the stopper inside vessel 11 is made of polystyrene or covered by (for example) extracellular matrix (ECM) 18. The device 10 is placed on a magnetic stirrer apparatus 19.

ECM is a matrix produced by endothelial cells such as corneal or vascular endothelial cells usually obtained from bovine or human sources. The ECM may be produced by culturing the cells inside said the vessel and then removing the cells after production of the ECM [Gospodarowicz D., et al., Endocr. Rev., 1:201-207 (1980)]. In addition, rather than using ECM, the surface may also be covered by various components thereof or artificially produced analogs which are capable of inducing the primary hemostasis, such as basement membrane matrix [e.g. MATRIGEL.TM., Flow Laboratories Inc., U.S.A.; Kleinman H., et al., Biochemistry, 25:312-318 (1986)], fibrilar or non-fibrilar collagen of various types, von Willebrand factor (VWF), fibronectin (Fib), etc. Alternatively the polystyrene may serve as an attractive surface to which plasma proteins like VWF and Fib. are attached and then they provide the surface to which platelets adhere [Savion. N. et al. Brit. J. Hematol., 112:1055-1061 (2001)].

It has now been realized that an apparatus as described in U.S. Pat. No. 5,523,238 may be used for managing coagulation disorders resulting from, e.g. coagulation dysfunction. The term "managing", as used above, denotes not only the detection of platelet-mediated coagulation diseases/disorders in a subject susceptible of having same, but also identification of the cause of the condition, as well as monitoring treatment of a subject with drugs specific to coagulation diseases/disorders.

Thus, according to a first aspect, the present invention provides a method for determining platelet-medicated clot formation in a blood sample comprising:
(a) obtaining a sample of blood, and optionally mixing same with an anti-coagulant in an amount effective to inhibit clot formation;
(b) in a vessel, mixing the sample with a minute amount of an initiator to obtain a mixed sample, the amount being effective to initiate coagulation;
(c) rotating the mixed sample inside the vessel, whereby shear forces are developed at the surface of said vessel in a manner and for a time sufficient to allow adhesion of platelets at the surface of said vessel;
(d) determining clot formation at the surface of said adherent platelets.

According to one specific embodiment of the invention, there is provided a method for determining a coagulation disorder in a subject having a coagulation factor dysfunction, the method comprising:
(a) obtaining from said subject a sample of blood, and optionally mixing same with an anti-coagulant in an amount sufficient to inhibit clot formation;
(b) in a vessel, mixing the sample with a minute amount of an initiator to obtain a mixed sample, the amount being sufficient to initiate coagulation;
(c) rotating the mixed sample inside the vessel, whereby shear forces are developed at the surface of said vessel in a manner and for a time sufficient to allow adhesion of platelets at the surface of said vessel;
(d) determining clot formation at the surface of said adherent platelets;
whereby a significant abnormal fibrin clot formation at said surface of adhered platelets indicating that said subject has a coagulation factor dysfunction.

This method also enables the determination of the concentration of the factor in the blood sample. Accordingly, a plurality of vessels are used in which increasing concentrations of the coagulation factor are added and a titration curve is thereby obtained. From the titration curve by comparison to results from a healthy subject, the concentration of the factor in the drug can be determined.

The term "abnormal fibrin clot formation" used herein above and below includes hypo-coagulation, hyper-coagulation as well as a condition when no statistically significant clots are formed at all, as compared to reference (standard) values of coagulation typically determined from samples from healthy subjects.

The term "statistically significant" or in short, "significant" as used herein above and below is determined by consideration and significance tests known to those versed in the art. A significance test is performed to determine if the observed value differs enough from a previously defined or a hypothisized value (termed herein "standard reference value"). The significance of a result is also called the p-value. According to the instant invention, abnormal clot formation is defined by a p-value less than 0.05 ($p<0.05$) from a standard value.

Contrary to commonly practiced methods for determining coagulation disorders, which are based on measuring the required time for a clot to form, the present invention is based on parameters of the clot per se, such as its size, surface coverage, and independent from the time of its formation.

The tested blood sample is preferably a whole blood sample, i.e. blood including all its cellular and protein components, or patient's plasma added to a donor's blood depleted of it's own plasma, the donor being a healthy subject, i.e. with no coagulation disorder.

The sample is optionally mixed with an anti-coagulant which is added in order to neutralize the effects of the hemostasis mechanism. Thus, the amount should be sufficient to inhibit coagulation and is standard practice. For example, for this purpose, sodium citrate, a commonly used anti-coagulant, is provided at a concentration of 0.32%-0.38%. However, it should be appreciated by those versed in the art that if the method of the invention is performed immediately after blood withdrawal, the use of anti-coagulant may be avoided.

According to this aspect, the initiator added to the sample inside the vessel in order to initiate clot formation. Coagulation initiators are known in the art and may be selected, for example, from thrombin, factor Xa, aPTT reagent, PT-fibrinogen reagent, $CaCl_2$. The "minute amount" of an initiator is determined by considerations known to those versed in the art. For example, when using factor Xa the concentration known to initiate coagulation is $1.0 \times 10^{-3}$ unit/ml.

At this stage the sample is rotated inside the vessel under shear forces developed as described in U.S. Pat. No. 5,523,238. The rotation of the fluid inside the vessel, and hence the shear forces, can be induced by a number of means. For example, the shear forces are produced by rotation of the vessel, in which case, the vessel is preferably cylindrical. Alternatively, the vessel may be stationary and the rotation of the fluid is produced by a rotating element inside the vessel. The rotating element may be cylindrical. In such a case, the shear forces acting inside the vessel gradually increase from the center of the vessel towards the periphery. Alternatively, the rotating element has the shape of an inverted cone.

The rotating element may be driven by a number of means, e.g. by direct mechanical coupling to a rotating motor or by means of magnetic coupling to an external magnetic driving means (e.g. a magnetic stirrer).

According to one embodiment of the invention, after the blood sample is placed within the vessel, the blood is rotated for a duration of 10 seconds to 10 mins., e.g. about 2 min., at a shear force of, which may for example be, in the range of 50-3000 $sec^{-1}$, preferably in the range of 100-2000 $sec^{-1}$.

The shear forces enable the adhesion of platelets at the surface of the vessel. If no platelets adhere at the surface the physician conducting the assay may conclude that the coagulation disorder results from platelet dysfunction. Thus, in order to determine abnormal platelet-mediated clot formation, the method of the invention stipulates that platelets adhere at said surface.

The adhesion of platelets onto the surface of the vessel and the formation of fibrin clots are determined by any of a number of means known per se such as optical inspection using a light microscope after appropriate staining, determining changes in light absorbance or transmission, etc. The determination may also involve image analysis using various image analysis systems (IAS). Prior to visualization, the vessel containing the sample may be washed and the fibrin clots formed are stained with a fibrin dye, such as May Gruenwald stain or specific immuno-(plastic) beads coupled to anti-fibrin antibodies.

The degree of clot formation may be determined quantitatively or qualitatively. For quantitative evaluation, the determination of clot formation may also employ an image analysis system, which is integrated in the system. By the use of an image analysis system, different parameters reflecting the degree of platelet-mediated clot formation can be determined. Such parameters include, without being limited thereto, percentage of total area covered by the clots (percent surface coverage, SC %), mean size of observed clots (average size, AS), surface coverage and average size of the clots respectively. These parameters can be used to indicate response-no response to a specific drug. These parameters may also measure the levels of a specific clotting factor through the use of reference wells.

The degree of clotting is compared with a standard reference value (defining a normal level of clot formation). The reference value may be defined by using blood samples from healthy subjects. When the degree of clotting is significantly lower than a reference value, the subject is suspected of having a coagulation factor deficiency. When the degree of clotting is significantly higher than a reference value, the subject is suspected of having a hyper-coagulation state. Both significantly high clot formation and significantly low clot formation are defined collectively by the term "abnormal clot formation"

Once a statistically significant abnormal platelet-mediated clot is observed, the method may be completed by determining, either qualitatively or quantitatively, the cause of the abnormal condition.

Thus, according to a second aspect, the present invention provides a method for identifying coagulation effector dysfunction in a subject having a coagulation disorder. The term "coagulation effector" refers both to a coagulation factor and to a coagulation inhibitor, including activated coagulation factor/inhibitor, component of a coagulation factor or inhibitor as well as activators of a coagulation factor or inhibitor, as well as any other substance known in the art to be involved in the coagulation cascade, the deficiency of which may affect the formation of platelet-mediated fibrin clots.

According to one embodiment, the coagulation effector is a coagulation factor and the method is for identifying coagulation factor deficiency (observed by statistically low degree of clot formation in the above method of the invention). According to this embodiment, the method comprises:

(a) obtaining from said subject a sample of blood, and optionally adding to said sample an anti-coagulant in an amount sufficient to inhibit clot formation;

(b) in a vessel, mixing the sample with a minute amount of an initiator to obtain a mixed sample, the amount being sufficient to initiate clot formation;

(c) adding to said mixed sample an amount of a coagulation factor suspected to be deficient in the sample, to obtain a treated sample, the amount being sufficient to achieve platelet-mediated fibrin clot formation;

(d) rotating said treated sample inside the vessel, whereby shear forces are developed at the surface of said vessel in a manner and for a time sufficient to allow adhesion of platelets at the surface of said vessel;

(e) determining platelet-mediated fibrin clot formation at the surface of said adherent platelets, where:
  i. a significant increase in fibrin clots formed at said surface as compared with a reference sample indicates that said disorder is associated with a deficiency in said coagulation factor;
  ii. an insignificant increase in fibrin clots formed at said surface as compared with a reference sample indicates that said disorder is associated with a deficiency in a another coagulation factor.

In a case where no substantial clotting is observed, the method of the invention is repeated with another coagulation factor employed in step (c).

The coagulation factor added to the sample, i.e. the deficiency of which is to be determined, is selected by considerations available to those versed in the art. For example, the first factor tested may be selected based on the initial results (e.g. from the determination method above). Alternatively, the tested factor may be suggested based on symptoms of the disease/disorder, the ethnic origin of the subject (which at time has correlation with a specific deficiency) and other factors. For example, an Ashkenazi Jew having a clotting dysfunction would be tested for a deficiency in factor XI (FXI).

Non-limiting examples of coagulation factors, the deficiency of which may be determined by the method of the invention, include, Factors VIII and IX (associated with hemophilia), Factors V, VII, X, and II, which are rarer than the hemophilias, but produce similar symptoms as well as Factor XI.

In a case where none of the tested factors is capable of inducing platelet-mediated clot formation, an inhibitor to a clotting factor is suspected to be the cause for the clotting disorder (such as an antibody in clotting disorders associated with acquired autoimmune diseases) or a deficiency/dysfunction in a component of the inhibitory system (i.e. the protein C system or a component thereof). In order to identify such an inhibitor, mixing studies are performed. In particular, a plasma sample of the patient is mixed with plasma depleted blood of a donor and the above assay is repeated. If clot formation is inhibited the conclusion is that the patient's plasma contains such an inhibitory antibody.

The method of the invention provides the determination of a disorder associated with dysfunction of a natural coagulation inhibitor, such as protein C, protein S, anti-thrombin III, or a component of the protein C system.

Thus, according to a third aspect, the invention provides a method for determining dysfunction of a coagulation effector being one of an activated coagulation inhibitor or a component thereof or an activator of a coagulation inhibitor, in a subject having a hyper-coagulation disorder, the method comprises:

(a) obtaining from said subject a sample of blood, and adding to said sample an anti-coagulant in an amount sufficient to inhibit clot formation;

(b) in a vessel, mixing the sample with an amount of an initiator to obtain a mixed sample, the amount being effective to initiate clot formation; and with an amount of said effector or an activator thereof or a coagulation inhibitor substrate, the amount being effective to inhibit clot formation when added to a normal blood sample (i.e. from a healthy subject);

(c) rotating said sample inside the vessel, whereby shear forces are developed at the surface of said vessel in a manner and for a time sufficient to allow adhesion of platelets at the surface of said vessel;

(d) determining platelet mediated fibrin clot formation at the surface of said adherent platelets, where an insignificant decrease in clots formed at said surface as compared to a reference sample indicates that said disorder is associates with an abnormal response to said effector.

The term "abnormal response to a coagulation effector" denotes in general a response which does not result in the formation of normal platelet mediated clot formation as compared to a reference sample obtained with whole blood from a healthy subject.

In case the selected activated inhibitor or activator does not result in a significant inhibition of clot formation, in comparison with a reference value, the method of the invention is repeated with another postulated inhibitor or activator or substrate of an inhibitor.

A non-limiting example of an activator or Protein C is protac (a venom used to activate protein C). According to a preferred embodiment of this method, an initiator is used in combination with $CaCl_2$.

Protein C system refers to a series of reaction also known as the protein C pathway. The importance of this pathway is seen in the occurrence of thrombosis in individuals with deficiencies/dysfunctions in elements of the pathway like protein C and its substrates such as coagulation factors V and VIII, factor V Leiden, protein S and others as well as a deficiency in a combination of these elements. Thus, this method also enables the determination of a condition involved in the presence of an abnormal form of factor V, factor V Leiden (a factor V mutation that is resistant to degradation by activated protein C).

According to one specific embodiment, the method of the invention provides means form determining inhibition of activated factor X (Xa) in a blood sample, preferably whole blood sample, the method comprising:

(a) obtaining from a subject a sample of blood, and adding to the sample an anti-coagulant in an amount effective to inhibit clot formation;

(b) in a vessel, mixing the blood sample with Xa, the amount of Xa being effective to induce clot formation (determined by a reference blood sample obtained from a healthy subject);

(c) rotating the sample inside the vessel, whereby shear forces are developed at the surface of said vessel in a manner and for a time sufficient to allow adhesion of platelets at the surface of said vessel;

(d) determining platelet medicated fibrin clot formation at the surface of the vessel, whereby a significant decrease in clots formed at the surface as compared to a standard reference value indicates that the subject has a condition associates with Xa inhibitory effect.

According to this embodiment, the standard reference value may be obtained by sampling a second blood sample, however, where no Xa is added to the sample. Accordingly, a "normal" clot will be induced.

According to a fourth aspect, the invention also provides a method for monitoring blood concentration of an anti-thrombotic drug, such as coumadin, heparin, anti Xa, hirudin as well as other direct thrombin inhibitors. To this end, a blood sample is titrated with the respective reagent needed for correcting the effect of the anti-thrombotic drug. The reagent according to this aspect of the invention may be a coagulation factor or any other agent having an effect on platelet-mediated clot formation, the activity of which is affected by the presence of a drug in a subject's blood. In the context of the following method, the reagent is term "a drug counter reagent".

According to this aspect the method comprises:

(a) obtaining from said subject a sample of blood;

(b) in vessels, titrating said sample with increasing amounts of a drug counter reagent;

(c) rotating the titrated sample in said vessels, whereby shear forces are developed at the surface of the vessel in a manner and for a time sufficient to allow adhesion of platelets at the surface of said vessel;

(d) determining a titration curve for said drug counter reagent, the titration curve defining a parameter associated with clot formation as a function of concentration of the drug-counter reagent;

(e) determining from said titration curve blood concentration of said anti-thrombotic drug. According to one specific embodiment, the concentration is determined by selecting the concentration at which the clot size or surface coverage correlates with a normal size/coverage of clots obtained from a healthy donor.

According to this aspect, the minimal concentration of the drug counter reagent at which a significant increase in fibrin clots at the surface of the adherent platelets are formed is determined by comparison with a standard reference titration curve. The minimal concentration at which there is a significant increase in fibrin clots (as determined by measuring any one of the defined parameters) correlates with the concentration of the drug in the subject's blood.

According to this aspect of the invention, the drug counter reagent may be, without being limited thereto, PTT-reagent (e.g. for monitoring blood levels of heparin), PT-reagent (e.g. for monitoring blood levels of coumadin), Factor Xa (e.g. for monitoring blood levels of anti-Xa drugs) and thrombin (for monitoring blood levels of specific thrombin inhibitors), as well as factor VIIa.

Yet further, the invention may also apply for designing treatment of a coagulation disorder in subject, the treatment comprises provided said subject with an amount of coagulation factor known as being deficient in said subject, the amount being effective to achieve clot formation.

According to this aspect the method comprises:

(a) obtaining from said subject a sample of blood;

(b) in vessels, titrating said sample with increasing concentrations of a coagulation factor;

(c) rotating the titrated sample in said vessels, whereby shear forces are developed at the surface of the vessel in a manner and for a time sufficient to allow adhesion of platelets at the surface of said vessel;

(d) determining a titration curve for said coagulation factor, the titration curve defining a parameter associated with clot formation as a function of concentration of the coagulation factor;

(e) designing treatment of said subject based on said titration curve.

As defined hereinabove, the parameters may be surface coverage and average size of the clots.

DESCRIPTION OF SOME SPECIFIC EXAMPLES

Example 1

Factor Xa Mediated Clot Formation

Bovine factor Xa was dissolved in normal saline containing 0.5% BSA to yield a stock solution of 7Units/ml. The stock solution was stored at $-20°$ C. in small aliquots. Before use, the aliquots were thawed at 37° C. and the factor Xa was diluted 1:100 in the saline BSA solution to obtain a solution containing 0.07 Units/ml. One µl of the diluted solution contained $7 \times 10^{-5}$ unit of factor Xa.

On the upper cap of a CPA well set attached to a magnetic stirrer were placed 1.5 µl of 1M $CaCl_2$ solution and 2 µl of the diluted factor Xa solution ($1.5 \times 10^{-5}$ U). As control, no factor Xa or $CaCl_2$ were added to the same blood sample.

The stirrer assembly was placed in a CPA well containing 130 µl of whole blood obtained from a healthy subject and spinning at about 750 rpm started immediately. After 2 minutes the spinning was stopped, the magnet and cap were removed from the well and the well was washed with tap water to remove all residual blood. The washed wells were stained using the biological stain, May-Gruenwald stain, and the clot surface coverage and clot average size were qualitatively determined using a microscope connected to an Image Analyzer, e.g.: Impact-R image analysis system, DiaMed, Switzerland.

FIG. 1A-1D show the results obtained. In particular, when no Factor Xa or $CaCl_2$ are added to the blood sample, a typical field of adherent platelets is formed, with no fibrin clot formation (FIG. 1A). In the presence of Factor Xa and $CaCl_2$ (at the indicated concentrations) normal fibrin clots are formed (FIG. 1B).

To examine whether the coagulation cascade is platelet mediated, blood depleted of platelets was used. In particular, platelet depleted blood was treated with Xa and $CaCl_2$ (as in FIG. 1C). However, as shown in FIG. 1C, no clots were formed. Thus, it was concluded that fibrin clot formation is dependent on adherent platelets and that the fibrin clots are generated on the surface of activated platelets, as shown by the confocal microscopy image of FIG. 1D.

An alternative assay includes applying normal blood sample to a plate, so as to create platelet covered surface, washing the plate and adding to the platelet covered plate a plasma sample of interest supplemented with a clotting initiator and sheared over the adherent normal platelets. This mode of testing may be applied for blood samples from patients with low platelet count, as well as for testing stored plasma samples.

Example 2

Determining Correlation between Surface Coverage/Clot Size and Concentration of Clot Initiator In this assay, increasing concentrations of thrombin, which promotes fibrin clot formation, were applied to normal blood samples. In particular, thrombin was placed on the tip of the rotating conical disc, in an amount yielding final concentration according to the points indicated in FIG. 3A and FIG. 3B. The conical disc was then applied in the well containing 130 µL of citrated whole blood, rotated at 720 rpm for two minutes followed by washing and staining of the well. For quantitative determination of fibrin clot formation image analysis (using Impact-R image analysis system, DiaMed, Switzerland) was performed.

Image analysis of the stained fibrin clots was performed expressing the amount of clot in terms of % of surface covered (SC, %), and the average size (AS, µm$^2$) of the stained clots.

FIG. 2A shows that there is a significant correlation ($R^2=0.9845$) between the average size of the fibrin clots and thrombin concentrations (International Units/ml).

Figure 2B:
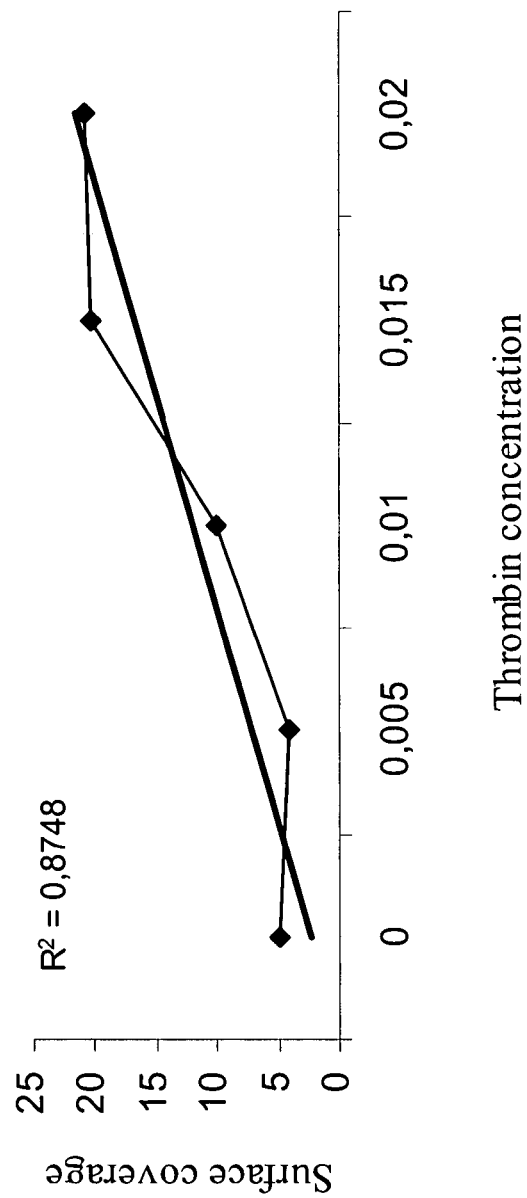

FIG. 2B shows that there is also a significant correlation ($R^2=0.8748$) between the surface coverage and thrombin concentrations.

Example 3

Use of the aPTT Reaction to Determine Factor VIII Deficiency

In the following assay undiluted aPTT reagent Diacelin (Daimed, Switzerland) was used to initiate clot formation. In particular, on the upper cap of a CPA well set attached to a magnetic stirrer 1.6 µl of 1M $CaCl_2$ and 3 µl of Diacelin were placed. The stirrer assembly was placed in a well containing 130 µl of whole blood and spinning at 720 rpm started immediately.

After 2.5 min. the spinning was stopped, the magnet and cap were removed from the well and the well washed with tap water to remove all residual blood. The washed wells were then stained using May-Gruenwald stain (Sigma) and clot % surface coverage and clot average size was quantitatively determined using an image analysis system (Impact-R).

FIG. 3A shows the results of the assay when no aPTT reagent or $CaCl_2$ were added to the blood. As a result, only single adsorbed platelets and platelet aggregates are shown, with no fibrin clots formation. Surface coverage of 7.4% and average clot size of 45 were determined using an image analysis system.

When the aPTT reagent and $CaCl_2$ were added as described above, extensive clot formation was obtained, with a surface coverage of 18.4% and average clot size of 104, demonstrating that clotting occurs in normal blood under these conditions (FIG. 3B).

Under the same conditions as above, however, with blood from hemophilia patients, no clot formation occurred in the presence of the aPTT reagent and $CaCl_2$ (FIG. 3C). In this specific case a surface coverage of 6.3% and average size of 36 were determined. These results also indicate that hemophilia patients, who are deficient of FVIII still, have a normal platelet adhesion under flow.

Further, when Hemate-P (a factor VIII concentrate) was added to the blood of the hemophilia patient to obtain a factor VIII level of about 1 unit/ml (normal level of FVIII), prior to the assay in the presence of the aPTT reagent and $CaCl_2$, extensive clotting was observed, similar to that obtained with normal plasma (FIG. 3D). In particular, a surface coverage of 21.3% and clot average size of 74 were determined.

Thus, by the above assay it is possible to determine factor VIII deficiency. In a similar manner, factor IX, factor XI (as well as other factors) deficiencies can be determined (using the respective factor concentrates).

Example 4

Use of a PT Reaction to Demonstrate Coumadin Use or Factor Deficiencies

In this assay PT-fibrinogen reagent (Instrumentation Laboratories) was diluted 1:10 in normal saline containing 0.5% BSA to yield a 10% solution. On the upper cap of a CPA well set attached to a magnetic stirrer 1.6 µl of 1M $CaCl_2$ and 3.8; or 4.0 µl of the diluted PT reagent were added.

The stirrer assembly was placed in a CPA well containing 130 µl of whole blood and spinning at about 720 rpm started immediately. The spinning was stopped after 2 min. The well was then washed and stained as described above, and clot % surface coverage and clot average size were determined.

FIG. 4A shows results with whole blood from healthy patients when no reagent or $CaCl_2$ were added (INR 1.3, INR being the ratio between PT clotting time of normal and of a tested plasma sample, with INR 0.8-1.3 representing a normal state while INR>1.4 representing an abnormal indicating the effect of coumadin or a missing factor usually FVII). As a result, only single adsorbed platelets and platelet aggregates are shown, with no fibrin clots formation.

FIG. 4B show the effect of addition of PT reagent and $CaCl_2$ to whole blood which resulted in the extensive formation of fibrin clots, with a surface coverage of 14.3% and clot average size of 115.

Similar conditions were applied to blood from patients receiving coumadin therapy (INR 3.0). FIG. 4C shows that in the absence of clot initiator or $CaCl_2$ no clots are formed, similar to the results obtained with whole blood from healthy subjects (FIG. 4A). When PT reagent was added to blood sample from coumadin treated patients, no clot formation was observed as well (FIG. 4D).

The above results indicate that the PT-based assay is sensitive to decreases in the vitamin K dependent clotting factors (II, VII, IX and X). This experiment was performed on blood from a patient on coumadin therapy where all the vitamin K dependent clotting factors are decreased (for an INR=3.0 they ranged between 25-40%). Thus, this assay may be useful also for identifying individual with congenital deficiencies of factors II, VII, IX or X, where the level of the deficient factor is 0-20% of normal.

Example 5

Heparin Inhibition of Factor Xa Clot Formation

In the following experiment bovine factor Xa (Sigma) and $CaCl_2$ were used to initiate clot formation in whole blood. On the upper cap of a CPA well set was placed 2.2 µl of a factor Xa solution ($7 \times 10^{-3}$ unit/ml) and 1.6 µl of 1M $CaCl_2$. The stirrer assembly was placed in a well containing 130 µl of whole blood and spinning at about 720 rpm started immediately. The spinning was stopped after 2 min. The well was then washed and stained, and the clot % surface coverage and the clot average size were determined.

FIG. 5A is an image obtained from whole blood from a healthy subject when no clot initiator (factor Xa or $CaCl_2$) was added. As a result, only single adsorbed platelets and platelet aggregates are shown, with no fibrin clots. Specifically, the surface coverage was 9.8% and clot average size 38. Similar results were obtained under the same conditions, however, with blood from a patient receiving heparin therapy (PTT=130 sec normal 26-34 sec), as presented in FIG. 5C. In this particular case, the surface coverage was 8.2% and clot average size 24.

However, when factor Xa and $CaCl_2$ were added to the blood from a healthy subject distinct fibrin clots were formed, with a surface coverage of 14.3% and clot average size of 115 (FIG. 5B). When the same assay was applied to blood from patient treated with heparin, no clot formation was observed, with a surface coverage of 3.0% and clot average size of 30 (FIG. 5D).

The above results indicate that this type of assay can be used to identify heparin use and that heparin levels could be determined by addition of measured amounts of polybrene or protamine sulfate, both being specific heparin inhibitors.

In a similar assay thrombin was used to initiate clot formation and the results obtained were similar to those with factor Xa (data not shown).

Example 6

Level of Synthetic Specific Factor Xa Inhibitors in Whole Blood

In the following experiment, the level of a synthetic factor Xa inhibitor was measured by titrating the inhibitor with known amounts of factor Xa. Factor Xa (9-11 µl of $7 \times 10^{-1}$ Units/ml or 2 µl of $7 \times 10^{-3}$ U/ml) and 1.6 µl of 1M $CaCl_2$ were placed on the upper cap of a CPA well set attached to a magnetic stirrer. The stirrer assembly was placed in a well containing 130 µl of whole blood and spinning at about 720 rpm started immediately. The spinning was stopped after 2 min and the well was washed and stained as described above. Clot surface coverage and clot average size was then determined.

FIG. 6A shows that when no inhibitor was added to the whole blood sample normal platelet deposition and aggregation occurred, with a surface coverage of 14% and clot average size of 45. However, when factor Xa ($1 \times 10^{-3}$ Units/ml) and $CaCl_2$ were added to a whole blood sample extensive clotting was observed (FIG. 6B) with a surface coverage of 16% and clot average size of 146.

When factor Xa and 1M $CaCl_2$ were added to blood of a patient receiving oral anti-factor Xa drug (Bayer), no clotting was observed (FIG. 6C), with a determined surface coverage of 6.6% and clot average size of 23.

When the patient's blood was treated with factor Xa ($4.5 \times 10^{-1}$ Units/ml) very slight clotting was observed (FIG. 6D) with a surface coverage of 2.1% and clot average size of 29. This low surface coverage may be explained by the low concentration of initiator used, which may result only in platelet activation without substantial clot formation (or at times even a reduction of the surface coverage). This is also evident from FIG. 3 showing the surface coverage in a dose response to thrombin. The surface coverage having a sort of an S-shape reflecting the initial trend for reduction of the surface coverage which at higher concentration is overcome.

The above results indicate that the concentration of the inhibitor in the patient's blood was $>4.4 \times 10^{-1}$ anti-Xa Units/ml. FIGS. 7E and 7F show that the extent of clotting in the patient's blood that was equivalent to the clotting of whole blood from the healthy subject containing $1 \times 10^{-3}$ Unit/ml of factor Xa occurred between $5.8 \times 10^{-1}$ and $6.4 \times 10^{-1}$ Units/ml of factor Xa. It was thus concluded that the level of the factor Xa inhibitor in the patient's whole blood was between $5.8 \times 10^{-1}$ and $6.4 \times 10^{-1}$ anti-Xa Units/ml.

The above results show that the method of the invention may be used to determine the levels of synthetic factor Xa inhibitors in a patient's whole blood and may therefore be used to monitor and manage drug therapy in these patients.

Example 7

Determination of the Levels of Specific Thrombin Inhibitors in Whole Blood

The levels of thrombin inhibitory drugs such as hirudin and its analogs were determined by titrating the thrombin inhibitor in a whole blood sample with thrombin. To a whole blood sample from a healthy subject hirudin (Sigma) was add to a level of $5 \times 10^{-1}$ anti-thrombin Units/ml. Bovine thrombin (Sigma) (5 Units/ml or 10 Units/ml) was then added to the hirudin treated and untreated whole blood. The thrombin was placed on the upper cap of a CPA well set attached to a magnetic stirrer. The stirrer assembly was placed in a well containing 130 µl of whole blood and spinning at about 720 rpm started immediately. After two min. the spinning was stopped. As described above, the well was washed and stained, and the clot % surface coverage and clot average size determined.

FIG. 7A shows that when no hirudin or thrombin is added to the whole blood, normal platelet deposition and aggregation occurs. The whole blood sample containing hirudin ($5\times10^{-1}$ antithrombin Units/ml) showed similar results (data not shown).

When thrombin was added to the whole blood containing hirudin, no clotting was observed at amounts expected to yield a thrombin concentration of $4\times10^{-2}$ Units/ml (FIG. 7B).

When thrombin was added to the whole blood, clotting began at an amount of added thrombin such that its concentration would have been $1\times10^{-2}$ Units/ml (FIG. 7C).

Clotting was observed when the added thrombin was at a concentration of $6\times10^{-2}$ Units/ml.

From the above results it was concluded that hirudin in the whole blood was able to inhibit between $3.5\times10^{-2}$ and $5\times10^{-2}$ Units/ml of thrombin. This is consistent with the level of $5\times10^{-2}$ antithrombin Units/ml of hirudin in the whole blood sample.

Thus, the above experiments demonstrate that as for factor Xa inhibitors clotting can also be used to monitor and manage anti-thrombin drug therapy.

The invention claimed is:

1. A method for determining platelet-mediated clot formation in a blood sample comprising:
   (a) obtaining a sample of blood, and optionally mixing the sample of blood with an anti-coagulant in an amount effective to inhibit clot formation;
   (b) mixing the sample of blood in a vessel with a minute amount of an initiator to obtain a mixed sample, the amount being effective to initiate coagulation;
   (c) rotating the mixed sample inside the vessel such that shear forces are developed at the surface of the vessel in a manner and for a time sufficient to allow adhesion of platelets at the surface of the vessel; and
   (d) determining fibrin clot formation at the surface of the adherent platelets.

2. The method of claim 1, wherein the sample of blood is a whole blood sample, a plasma sample, or a mixture of the plasma sample and a whole blood sample obtained from a healthy subject.

3. The method of claim 1, wherein clot formation is determined by a determination of a parameter selected from the group consisting of vessel's surface coverage (SC) by the clots and average size (AS) of the clots.

4. The method of claim 1, wherein a significant decrease in clot formation indicates a deficiency in a coagulation factor or an autoimmune disorder.

5. The method of claim 1, wherein a significant increase in clot formation indicates a deficiency in a coagulation inhibitor or activator of a coagulation inhibitor.

6. A method for determining a coagulation disorder in a subject having a coagulation factor dysfunction, comprising:
   (a) obtaining from the subject a sample of blood, and optionally mixing same with an anti-coagulant in an amount effective to inhibit clot formation;
   (b) mixing the sample of blood in a vessel with a minute amount of an initiator to obtain a mixed sample, the amount being effective to initiate coagulation;
   (c) rotating the mixed sample inside the vessel, whereby shear forces are developed at the surface of the vessel in a manner and for a time sufficient to allow adhesion of platelets at the surface of the vessel;
   (d) determining platelet-mediated fibrin clot formation at the surface of the adherent platelets;
   whereby a significant abnormal fibrin clot formation at the surface of the adhered platelets indicates that the subject has a coagulation factor dysfunction.

7. A method for identifying a coagulation effector dysfunction in a subject having a coagulation disorder, the method comprising:
   (a) obtaining from the subject a sample of blood, and optionally adding to the sample of blood an anti-coagulant in an amount effective to inhibit clot formation;
   (b) mixing the sample in a vessel with a minute amount of an initiator to obtain a mixed sample, the amount being effective to initiate clot formation;
   (c) adding to the mixed sample, an amount of a coagulation effector sufficient to affect platelet-mediated fibrin clot formation, the coagulation effector suspected of being deficient the group consisting of and selected from the group consisting of a coagulation factor, an activated coagulation inhibitor, a component of a coagulation inhibitor and an activator of a coagulation inhibitor, to obtain a treated sample;
   (d) rotating the treated sample inside the vessel, whereby shear forces are developed at the surface of the vessel in a manner and for a time sufficient to allow adhesion of platelets at the surface of the vessel; and
   (e) determining platelet-mediated fibrin clot formation at the surface of the adherent platelets, the clot formation in the sample being indicative that the dysfunction is associated with the coagulation effector.

8. The method of claim 7, wherein the blood sample is whole blood or plasma sample, the plasma sample optionally mixed with a whole blood sample obtained from a healthy subject.

9. The method of claim 7, wherein fibrin clot formation is determined by determination of a parameter selected from the group consisting of vessel's surface coverage by the clots and average size of the clots.

10. The method of claim 7, wherein the coagulation effector is a coagulation factor and the method further comprises determining an increase in platelet mediated fibrin clot formation, and wherein a significant increase in fibrin clots formed at the surface of the adherent platelets as compared with a reference sample, indicates that the disorder is associated with a deficiency in the coagulation factor.

11. The method of claim 10, further comprising placing a plurality of samples in respective plurality of vessels, and adding the coagulation factor in increasing concentrations to establish a titration curve for the coagulation factor.

12. The method of claim 7, for identifying a deficiency in a coagulation factor selected from Factors II, V, VII, VIII, IX, X, XI, XIII.

13. The method of claim 7, wherein the coagulation effector is selected from the group consisting of an activated coagulation inhibitor, a component of a coagulation inhibitor and an activator of a coagulation inhibitor, and the method includes determining a decrease in platelet mediated fibrin clot formation, where an insignificant decrease in clots formed at the surface of the adherent platelets as compared to a reference sample where no coagulation effector is added, indicates that the disorder is associated with an abnormal response to the effector.

14. The method of claim 13, wherein the coagulation effector is selected from the group consisting of protein C, protein S and anti-thrombin III.

* * * * *